(12) United States Patent
Hahn et al.

(10) Patent No.: US 6,944,571 B2
(45) Date of Patent: Sep. 13, 2005

(54) METHOD AND APPARATUS OF ESTIMATING PURE SPECTRA AND A CONCENTRATION OF A MIXTURE

(75) Inventors: Sangjoon Hahn, Seoul (KR); Haemin Cho, Yongin (KR); Gilwon Yoon, Seoul (KR); Kye-jin Jeon, Suwon (KR); In-duk Hwang, Suwon (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 53 days.

(21) Appl. No.: 10/667,131

(22) Filed: Sep. 22, 2003

(65) Prior Publication Data

US 2004/0148106 A1 Jul. 29, 2004

(30) Foreign Application Priority Data

Jan. 27, 2003 (KR) ................. 10-2003-0005198

(51) Int. Cl.$^7$ ............... G06F 19/00; G06F 15/00
(52) U.S. Cl. ............. 702/179; 702/30; 702/56; 702/189; 702/196
(58) Field of Search .............. 702/22, 28, 30, 702/56, 179, 189, 190, 196; 250/339.09, 339.12; 704/500, 501

(56) References Cited

U.S. PATENT DOCUMENTS 5,121,337 A * 6/1992 Brown ................. 702/28
6,321,200 B1 * 11/2001 Casey ................. 704/500

OTHER PUBLICATIONS

Chen et al "A New Approach to Near–Infrared . . . ". J. Chem. Inf. computer Sci., 41 (4): pp. 992–1001; dated 2001.*
Setarehdan et al., "Variable Selection for Partial . . . ", Applied Spectroscopy 56(3):337–345 (2002).
Steinbock et al., "A Demonstration of Principal . . . ", Analytical Chemistry, 69(18):3708–3713 (Sep. 1997).

* cited by examiner

*Primary Examiner*—Bryan Bui
(74) *Attorney, Agent, or Firm*—Lee & Morse, P.C.

(57) ABSTRACT

A method of estimating a pure spectrum and a concentration of each component constituting n sample mixtures, in which p kinds of components are mixed, includes (a) performing a principal component analysis of the spectra of the n mixtures, which are measured using m wavelengths, to represent the spectra of the n mixtures as factors and scores of the respective factors, wherein n, p, and m are integers and m>p, and (b) performing an independent component analysis of the scores obtained in (a) to estimate the pure spectra and the concentrations of the respective components.

13 Claims, 7 Drawing Sheets

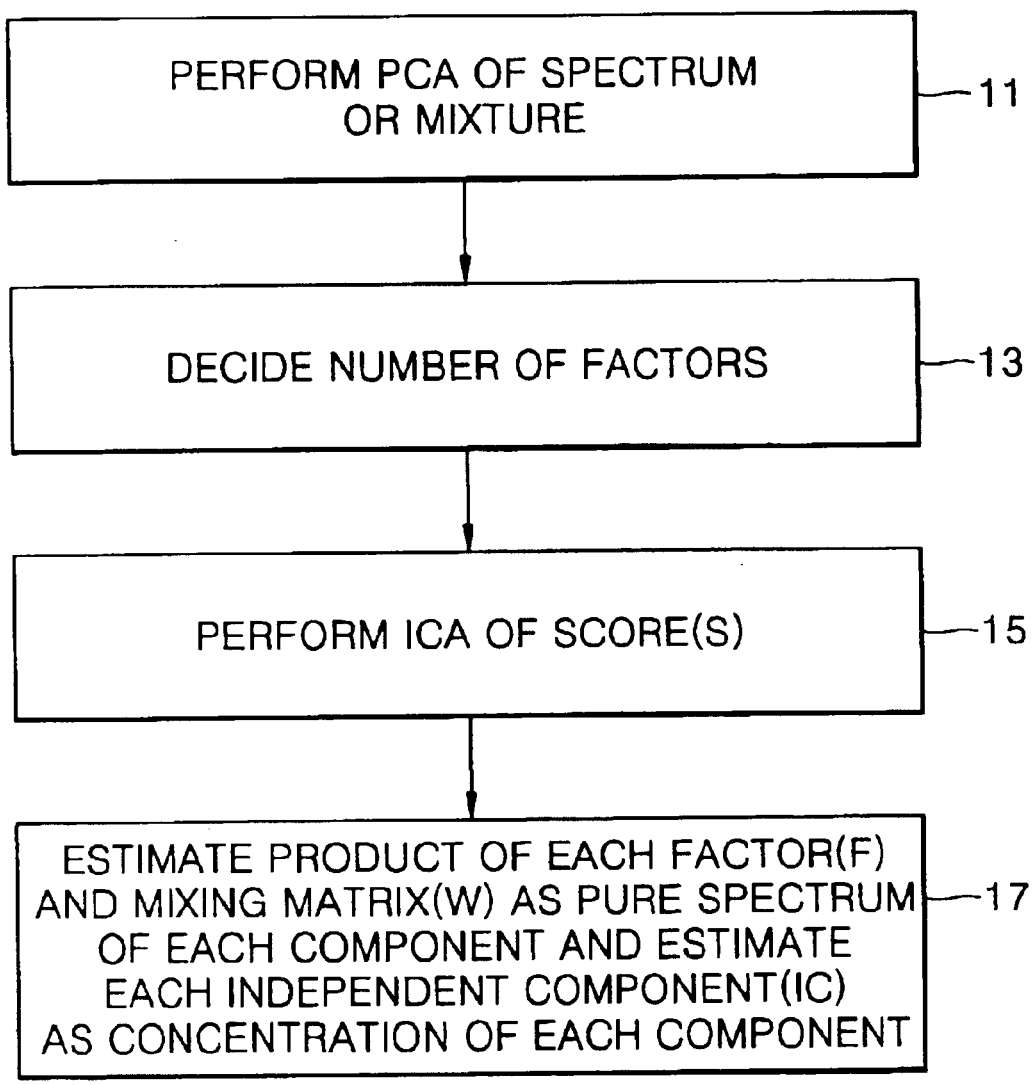

SUCROSE

GLUCOSE

METHOD AND APPARATUS OF ESTIMATING PURE SPECTRA AND A CONCENTRATION OF A MIXTURE

BACKGROUND OF THE INVENTION

1. Field of the Invention

The present invention relates to a spectral analysis of mixtures. More particularly, the present invention relates to a method and apparatus of estimating a pure spectrum and a concentration of each component constituting a mixture by performing a principal component analysis and an independent component analysis of the spectrum of the mixture.

2. Description of the Related Art

A principal component regression (PCR) is generally used to estimate a concentration of a spectrum of a mixture. PCR is a multivariate analysis including two steps. The first step is a principal component analysis (PCA), in which the measured spectrum of a mixture is decomposed into a product of a factor and a score using singular value decomposition (SVD). Typically, because the factor and the score, obtained by the SVD, do not exactly match the pure spectrum and the concentration, it is difficult to estimate the pure spectra and the concentration from the spectrum of the mixture using only PCA. For this reason, to estimate the concentration, PCR requires information in addition to the spectrum of the mixture, i.e., information on the concentration of the mixture. In the second step, the additional information, i.e., the concentration of the mixture, is regressed into the score produced by the PCA to obtain a regression vector. The regression vector, obtained from a regression equation of the score and the concentration, is a contravariant vector of pure spectra of components other than a particular component to be estimated in the mixture. However, the regression vector does not exactly match the pure spectrum of the particular component. Although the regression vector obtained by PCR enables estimation of the concentration of a particular component from the spectrum of a mixture, it is still difficult to estimate the pure spectrum of the particular component.

Consequently, it is impossible to estimate the pure spectrum of each component contained in a mixture using PCR. In addition, to estimate the concentration of each component, PCR requires an additional calibration set including accurate information on the concentration of the mixture. Further, in a case where only the information on the spectrum of a mixture is given because calibration is actually impossible, the multivariate analysis cannot be employed.

SUMMARY OF THE INVENTION

The present invention provides a method and apparatus of estimating a pure spectrum and a concentration of each component of a mixture using only the spectrum of the mixture by applying a principal component analysis (PCA) and an independent component analysis (ICA) to the spectrum of the mixture.

In accordance with an embodiment of the present invention, a method of estimating a pure spectrum and a concentration of each component constituting n sample mixtures in which p kinds of components are mixed includes (a) performing a principal component analysis of the spectra of the n mixtures, which are measured using m wavelengths, to represent the spectra of the n mixtures as factors and scores of the respective factors, wherein n, p, and m are integers and m>p, and (b) performing an independent component analysis of the scores obtained in (a) to estimate the pure spectra and the concentrations of the respective components.

Preferably, the number of factors to be used is decided from among the factors obtained in (a) and the independent component analysis is applied to the scores of the decided factors. The concentrations of the components constituting the mixture may be statistically independent.

Performing the independent component analysis may include (b1) performing the independent component analysis of the scores of the factors to decompose the scores into a mixing matrix and independent components, (b2) estimating the product of the factors obtained in (a) and the mixing matrix obtained in (b1) as the pure spectra of the respective components, and (b3) estimating the independent components obtained in step (b1) as being proportional to the concentrations of the components contained in the mixture.

Performing the independent component analysis may include (b1) (b1) deciding the number of the factors to be used from among the factors obtained in (a), (b2) performing the independent component analysis of the scores of the decided factors to decompose the scores into a mixing matrix and independent components, (b3) estimating the product of the decided factor and the mixing matrix obtained in (b2) as the pure spectrum of each component, and (b4) estimating the independent components obtained in (b2) as being proportional to the concentrations of the components contained in the mixture.

In accordance with another embodiment of the present invention, there is provided a computer-readable medium having embodied thereon a first program for performing a principal component analysis of a spectra of the n mixtures measured using m wavelengths to represent the spectra as factors and scores of the respective factors, wherein n and m are integers, and a second program for performing an independent component analysis of the scores produced by the first program to decompose the scores into a mixing matrix and independent components, estimating that the product of the factor obtained by the first program and the mixing matrix is the pure spectra of each component, and estimating that the independent components are proportional to the concentrations of the components contained in the mixture.

In accordance with still another embodiment of the present invention, an apparatus of estimating a pure spectrum and a concentration of each component constituting n sample mixtures, in which p kinds of components are mixed includes a principal component analysis unit for performing a principal component analysis of the spectra of the n mixtures, which are measured using m wavelengths, to represent the spectra of the n mixtures as factors and scores of the respective factors, where n, m, and p are integers and m>p, an independent component analysis unit for performing an independent component analysis of the scores provided from the principal component analysis unit, to decompose the scores into a mixing matrix and independent components, a pure spectrum estimating unit for estimating the product of the factor provided from the principal component analysis unit and the mixing matrix as the pure spectra of each component, and a concentration estimating unit for estimating the independent components as the concentrations of the components contained in the mixture.

BRIEF DESCRIPTION OF THE DRAWINGS

The above and other features and advantages of the present invention will become more apparent to those of ordinary skill in the art by describing in detail preferred embodiments thereof with reference to the attached drawings in which:

FIG. 1 is a flowchart illustrating a method of estimating pure spectra and concentrations of each component constituting a mixture according to a preferred embodiment of the present invention;

DETAILED DESCRIPTION OF THE INVENTION

Figure 2A:
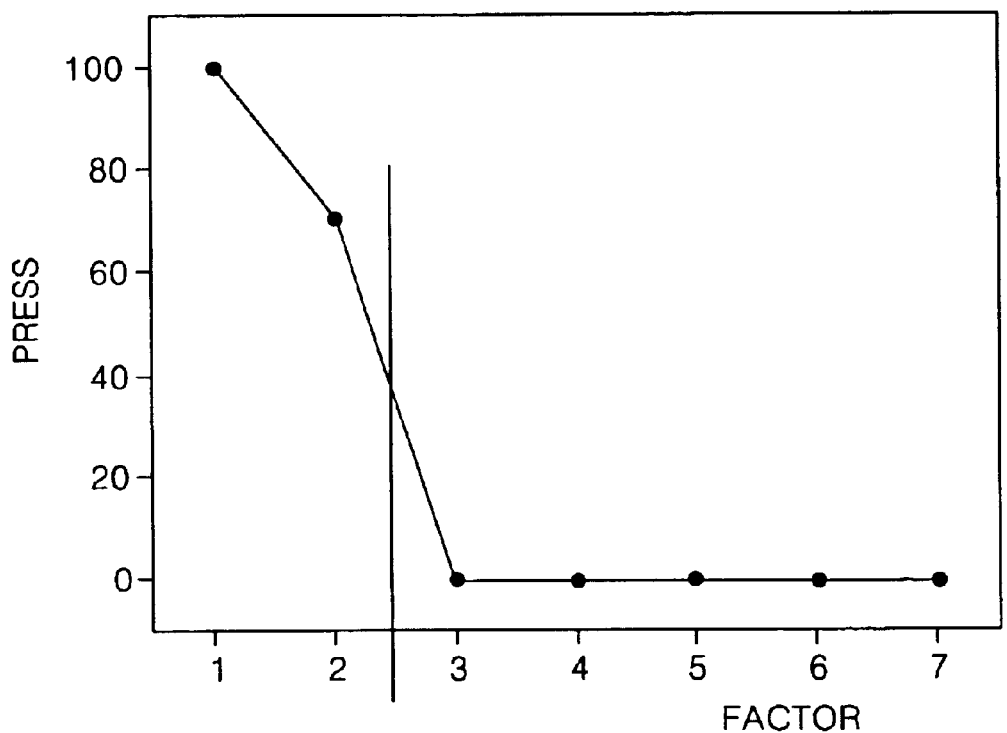
FIGS. 2A through 2C are graphs showing a relationship of each factor and a press for explaining step 13 as shown in FIG. 1.

Korean Patent Application No. 2003-5198, filed on Jan. 27, 2003, and entitled: "Method and Apparatus of Estimating Pure Spectra and a Concentration of a Mixture," is incorporated by reference herein in its entirety.

The present invention will now be described more fully hereinafter with reference to the accompanying drawings, in which preferred embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

A spectrum of a mixture may be expressed as a linear combination of the spectra of components contained in the mixture as shown in Equation (1):

$$A_w = A_{a,w} + A_{b,w} + A_{c,w} \quad (1)$$

where $A_w$ represents a spectrum of a mixture measured using a wavelength w, and $A_{a,w}$, $A_{b,w}$, and $A_{c,w}$ represent spectra of components a, b, and c, respectively, measured using a wavelength w.

Meanwhile, a spectrum of each component may be expressed as the product of a pure spectrum and concentration as shown in Equation (2):

$$A_{c,w} = K_{c,w} \times C_c \quad (2)$$

where $A_{c,w}$ represents the spectrum of component c measured using a wavelength w, $K_{c,w}$ represents the pure spectrum of the component c, measured using a wavelength w, and $C_c$ represents the concentration of the component c.

From Equations (1) and (2), the spectrum of the mixture can be expressed as Equation (3):

$$A_w = K_{a,w} \times C_a + K_{b,w} \times C_b + K_{c,w} \times C_c \quad (3)$$

In addition, in a case where several mixtures are produced by mixing respective components with different concentrations, the spectrum of one of the mixtures can be expressed as Equation (4):

$$A_{w,n} = K_{a,w} \times C_{a,n} + K_{b,w} \times C_{b,n} + K_{c,w} \times C_{c,n} \quad (4)$$

where $A_{w,n}$ represents the spectrum of the $n^{th}$ mixture measured using a wavelength w, $K_{a,w}$, $K_{b,w}$, and $K_{c,w}$ represent the pure spectra of components a, b, and c, respectively, measured using a wavelength w, and $C_{a,n}$, $C_{b,n}$, and $C_{c,n}$ represent the concentrations of the components a, b, and c, respectively, of the $n^{th}$ mixture.

Equation (4) can be expressed in a matrix form as shown in Equation (5):

$$A = M \cdot C \quad (5)$$

That is, the spectrum A of a mixture can be expressed by the products of the pure spectra M and the concentrations C of the components thereof. Here, when the number of mixtures is n, the number of wavelengths at which the spectra of mixtures are measured is m, and the number of components is p, where n, m, and p are integers, and m>p, the dimension of matrix A is (m,n), the dimension of matrix B is (m,n), and the dimension of matrix C is (p,n).

Hereinafter, the present invention will be described in detail based on spectral characteristics of mixtures.

FIG. 1 is a flowchart illustrating a method of estimating the pure spectrum and the concentration of each component from the spectrum of a mixture according to a preferred embodiment of the present invention. Preferably, the method includes, in step 11, performing a principal component analysis (PCA), in step 13, deciding the number of factors, in step 15, performing an independent component analysis (ICA), and, in step 17, estimating the pure spectra and concentration.

Referring to FIG. 1, in step 11, the measured spectrum A of the mixture is analyzed using the PCA and is decomposed into basic variates. For this, in step 11, singular value decomposition (SVD) is applied to the measured spectrum A of the mixture and decomposes the spectrum A into the product of a factor F and a score S as shown in Equation (6):

$$A = USV' = FS \quad (6)$$

where the factor F is the common variate of the spectrum A of the mixture and denotes an eigenvector or a principal component. The score S denotes a scaling coefficient corresponding to each principal component.

Supposing that the number of the mixtures is n, the number of the wavelengths at which the spectrum of the mixture is measured is m, and the number of the components is p, the dimension of matrix A is (m,n), U is an orthogonal matrix of dimension (m,m), V is an orthogonal matrix of dimension (n,n), and S is a diagonal matrix of dimension (m,n), which consists of singular values whose covariance $\sigma_{ij}$ (where i≠j) is zero (0). Meanwhile, the dimension of the factor F is (m,p), while the dimension of the score S is (p,n). Referring to Equation (6), it may be seen that the factor F is US, and the score S is V'. That is, according to the PCA, principal components occupying a large portion (e.g., 80% to 90%) of total variance of original variables are decided as optimum factors to be used in the next step. Subsequently, other components occupying a smaller portion may be regarded as noise and removed. Thus, the score obtained by the PCA no longer has correlation.

Meanwhile, in a case where the SVD is applied to the pure spectrum as shown in Equation (5), we suppose that the pure spectrum M can be expressed as in Equation (7):

$$M = usv' \quad (7)$$

where, when the concentrations of the components contained in the mixture are statistically independent, because a covariance matrix of the concentration C as shown in Equation (5) becomes a unit matrix, Equation (8) is obtained based on Equations (6) and (7) as follows:

$$U=u, \ S=s, \ V'=v'C \quad (8)$$

Accordingly, the factor F, the score S, the pure spectrum M, and the concentration C are in a relationship as shown in Equation (9):

$$M=usv'=USv'=Fv'$$
$$C=(v')^{-1}V'=(v')^{-1}S$$
$$S=v'C \quad (9)$$

More specifically, the pure spectrum M is obtained by multiplying the factor F by matrix v', and the concentration C is obtained from the score S multiplied by $(v')^{-1}$.

Meanwhile, before performing the PCA in step 11, a low-noise band including information on a component to be estimated among the spectra of the n mixtures measured using the m wavelengths is decided as an analysis band. For this, the spectrum is recomposed from the score S and the factor F, which are calculated by the PCA. Next, a difference (i.e., a residual) between the recomposed spectrum and the initial spectrum A is calculated. Thus, a range having a larger residual is normally decided as a high-noise range. In addition, before performing the PCA in step 11, the spectra of the n mixtures undergo data preprocessing, such as multiplicative scatter correction (MSC), mean-centering, and autoscaling, in order to remove scattering and noise contained in the spectra of the human tissue.

Figure 2B:
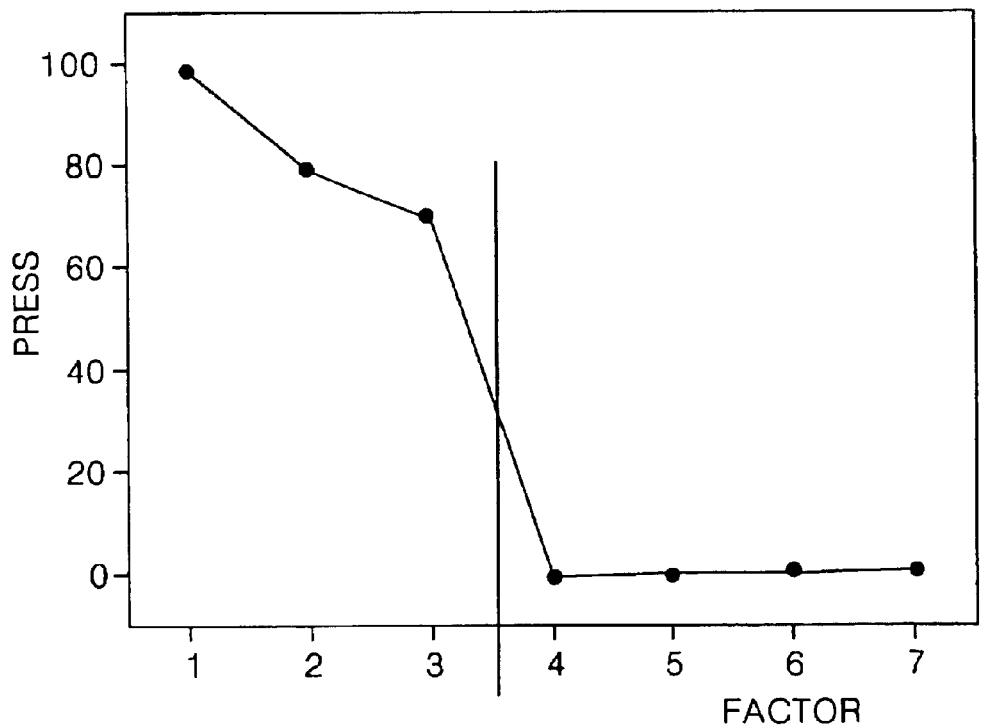
Figure 2C:
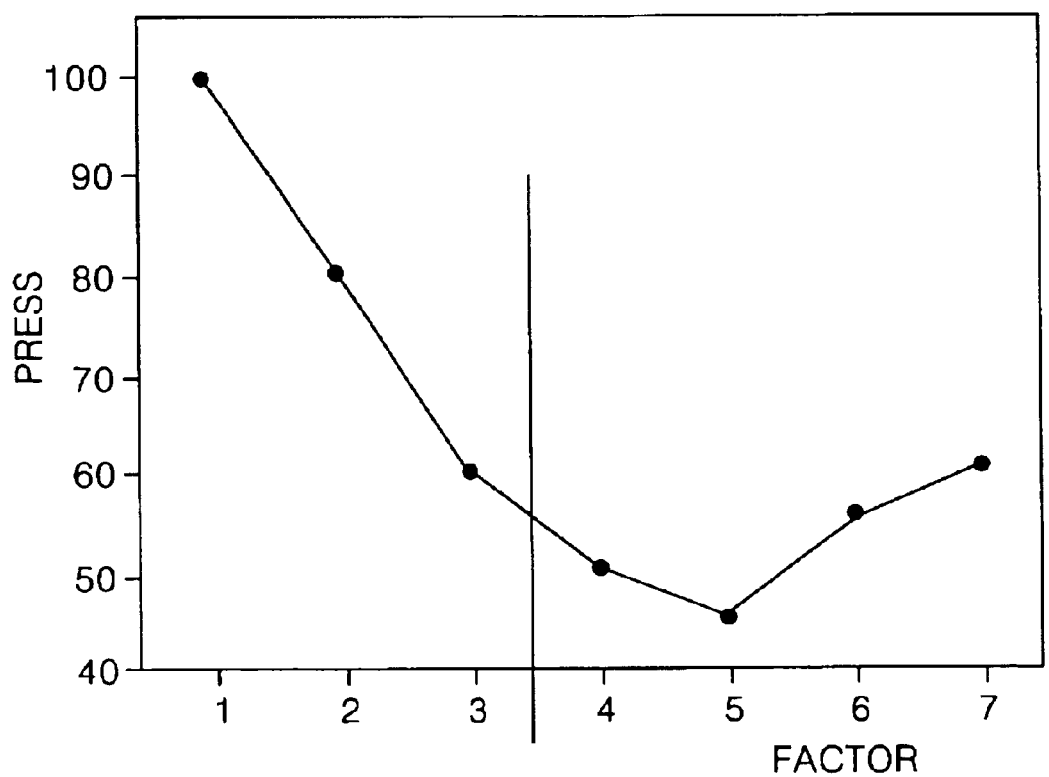

In step 13, the number of factors to be used for performing independent component analysis in step 15 is decided from among the factors F produced by the PCA in step 11. Step 13 will be described in detail with reference to FIGS. 2A through 2C. FIGS. 2A and 2B are graphs showing a relationship between each factor and a press when there is no noise. FIG. 2C is a graph showing a relationship between each factor and the press when there is a noise.

In step 13, a statistic called "press" of each factor F produced by step 11 is calculated. If there is no noise, it is possible to estimate the number of components constituting a mixture using only the press. That is, in a case where there is no noise, as shown in FIGS. 2A and 2B, the numbers of factors F that have a non-zero press corresponds to the number of principal components contained in a mixture. Thus, it may be seen that the mixtures contain two (2) and three (3) components, respectively.

However, since there generally is noise, as shown in FIG. 2C, the press does not exactly have the value zero (0). In this case, a position where the press is taken to be as zero (0) is statistically estimated using an F-test. Specifically, to perform the F-test, an f-ratio is obtained using Equation (10):

$$F_k = \frac{PRESS_k - PRESS_{\min}}{PRESS_{\min}} \cdot \frac{n}{n-k} \quad (10)$$

where $F_k$ is the f-ratio of a $k^{th}$ factor, $PRESS_k$ is the press value of the $k^{th}$ factor, $PRESS_{min}$ is the minimum press value, and n is the number of the measured spectra.

Next, the f-value of each factor F is obtained using the f-ratio as a parameter. Finally, it is estimated that the number of the factors, of which f-values are more than 0.95, is equal to the number of components contained in a mixture. Here, the value "0.95" is selected considering that the general estimation reliability is 95%.

In step 15, i.e., performing the ICA to obtain the matrix v' using Equation (9), even statistics of third or higher order, which are not used in the step of performing the PCA, are made to be statistically independent. More specifically, in a case where the concentrations C are statistically independent at a higher order, non-zero values are positioned only on the diagonal in a statistical multidimensional tensor of the concentrations C, while zero (0) is positioned at other portions. Meanwhile, as the score S obtained by the PCA equals v'C, even if v' is orthogonal, non-zero values may be positioned on portions other than the diagonal in a multidimensional tensor of the v'C unlike that of the concentrations C. Thus, a multidimensional tensor is obtained by rotating the score S to find a rotation v' by which the value zero (0) is positioned only on the diagonal.

In step 15, the ICA is applied to the score S obtained in step 11, preferably, the score S of the factor F decided in step 13, thereby decomposing the score S into a mixing matrix W and independent components (ICs) as shown in Equation (11):

$$S=W \cdot IC \quad (11)$$

wherein it is supposed that the number of mixtures is n, the number of components is p, the dimension of the score S is (p,n), and the dimension of the independent components is (p,n).

In step 15, the ICA may be performed using maximization of non-gaussianity (MN), maximum likelihood estimation (MLE), minimization of mutual information (MMI), or the like. Specifically, the algorithm "fastICA" of Hyvärinen may be used.

Meanwhile, both Equation (9) and Equation (11) express the score S decomposed into two matrixes. Also, though IC and C are expressed in different forms, the ICA is performed on the assumption that if IC and C have the same statistics, IC is identical to C. Here, the statistic includes not only second-order statistics used in the PCA but also higher-order statistics used in the ICA. Therefore, even if the second-order statistics of the score S obtained in the PCA are equal to the second-order statistics of C, it cannot be inferred that the two quantities are equal. However, if the higher-order statistics of the score S obtained in the PCA is equal to the higher-order statistics of IC obtained in the ICA, the two quantities may then be decided as equal. The present invention is described on the assumption that the concentrations C of respective components are statistically independent, and the independent components IC obtained in the ICA are also independent. Therefore, the concentration C and the independent component C may be commonly used to express physical quantities and are proportional to one another. That is, the concentration C can be expressed as C=proportionality IC. As a result, v' and W in Equation (9) and Equation (11), are proportional to one another.

In step 17 of estimating pure spectrum and concentration, substituting Equation (11) obtained in step 15 into Equation (11) results in the following Equation (12):

$$A=F \cdot S=F \cdot W \cdot IC \quad (12)$$

Consequently, referring to Equation (12), it is estimated that the product of the factor F and the mixing matrix W is the pure spectrum W of each component, and that the independent components C are proportional to the concentrations of the components contained in the mixture.

Figure 7:
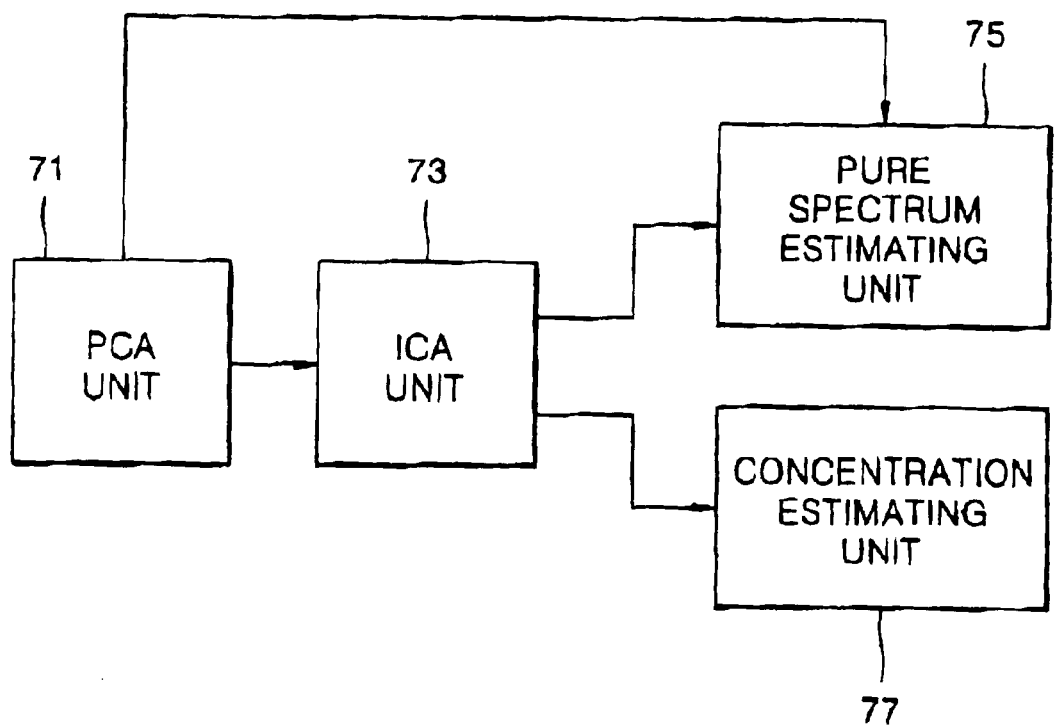
FIG. 7 is a block diagram of an apparatus of estimating pure spectra and concentrations of a mixture according to a first embodiment of the present invention.

FIG. 7 is a block diagram of an apparatus of estimating pure spectra and concentrations of each component constituting a mixture according to a preferred embodiment of the present invention.

Referring to FIG. 7, the apparatus includes a principal component analysis (PCA) unit 71, an independent component analysis (ICA) unit 73, a pure spectrum estimating unit 75 and a concentration estimating unit 77.

The PCA unit 71 performs a principal component analysis of the spectra of the n mixtures, which are measured using m wavelengths, to represent the spectra of the n mixtures as factors and scores of the respective factors. The ICA unit 73 performs an independent component analysis of the scores provided from the principal component analysis unit to decompose the scores into a mixing matrix and independent components. The pure spectrum estimating unit 75 estimates the product of the factor provided from the principal component analysis unit and the mixing matrix as the pure spectra of each component. The concentration estimating unit 77 estimates the independent components as the concentrations of the components contained in the mixture.

Exemplary Embodiment

Twenty-five (25) sample water solutions, which were made by mixing glucose and sucrose with different concentrations, underwent PCA and then ICA. The pure spectrum of each of the glucose and sucrose is shown as FIG. 3. The spectra of the twenty-five (25) mixtures made by mixing the glucose and the sucrose with different concentrations are shown in FIG. 4.

Figure 3:
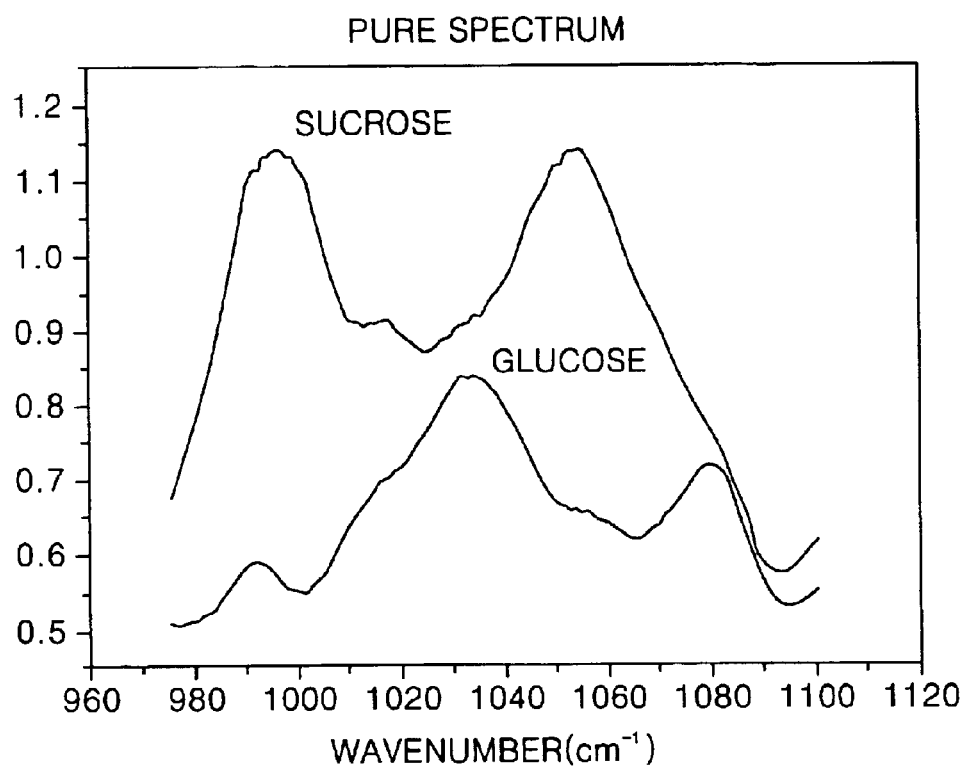
FIG. 3 shows pure spectra of sucrose and glucose.
Figure 4:
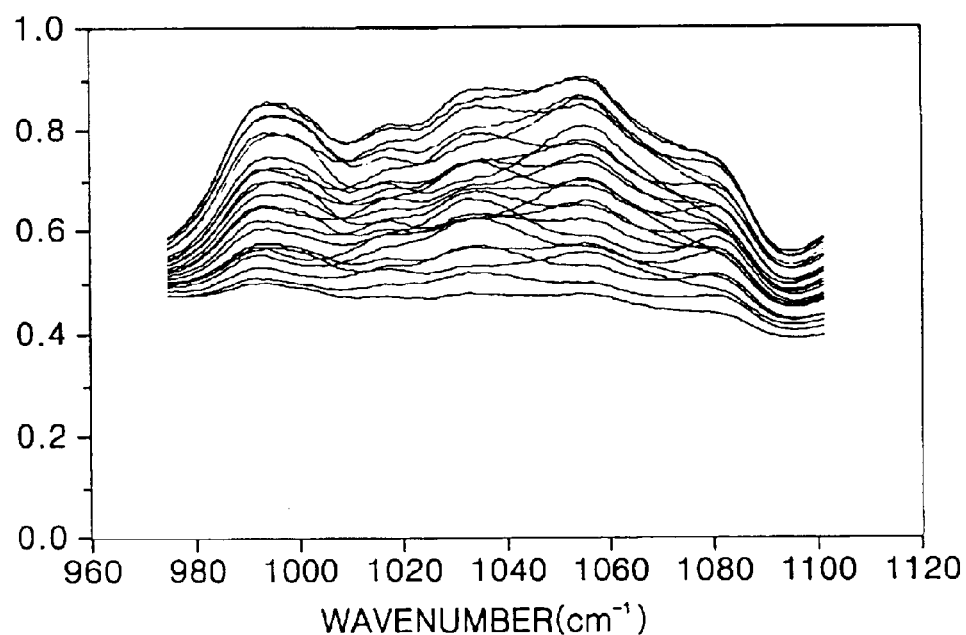
FIG. 4 shows spectra of twenty-five (25) mixtures produced by mixing sucrose and glucose with different concentrations.
Figure 5A:
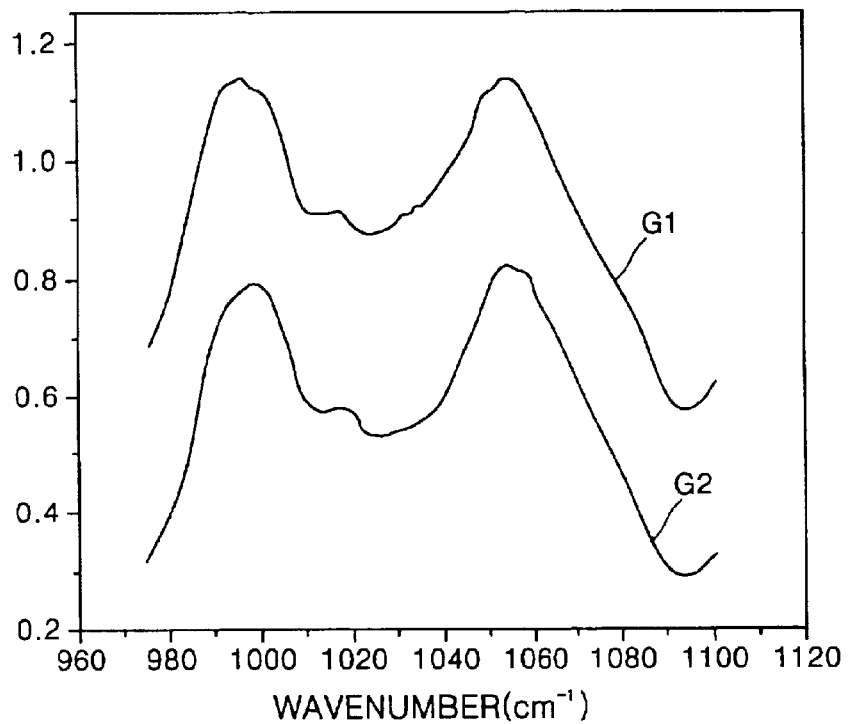
FIGS. 5A and 5B show pure spectra of sucrose and glucose obtained by applying the present invention to the spectra of the mixtures shown in FIG. 4.
Figure 5B:
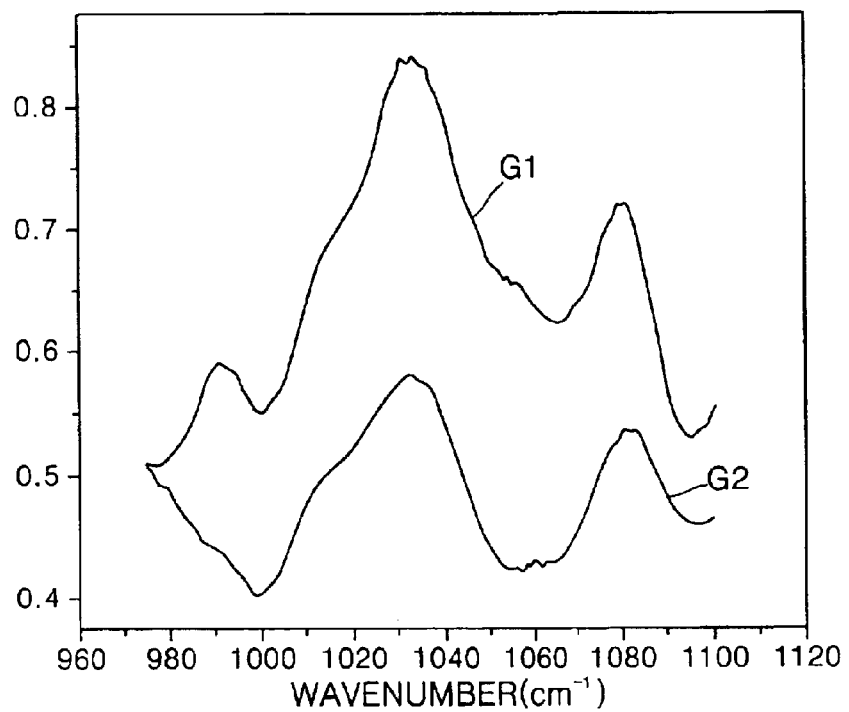
Figure 6A:
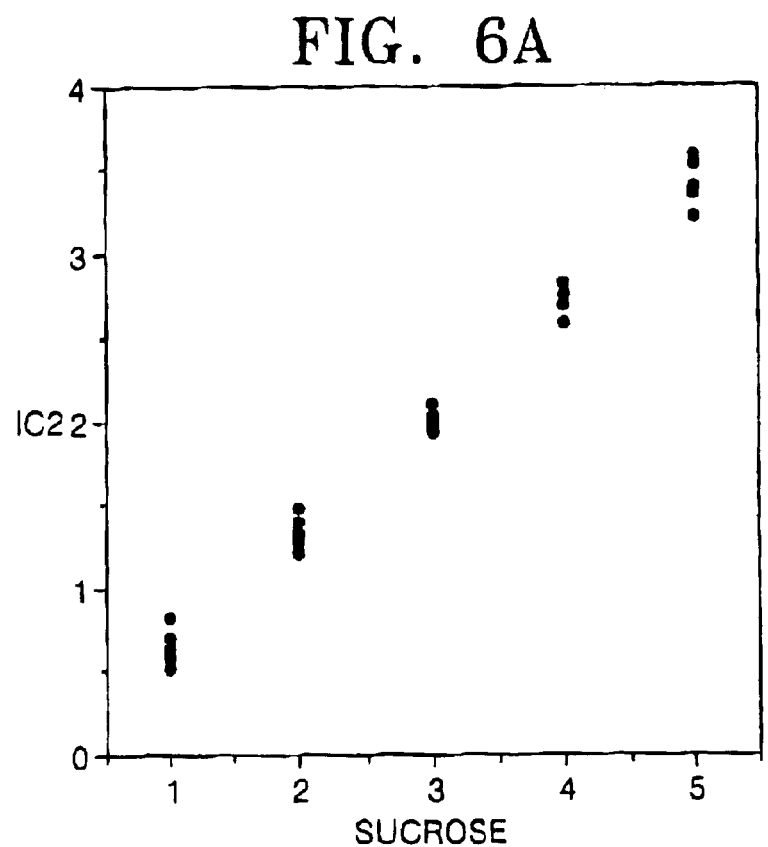
FIGS. 6A and 6B show concentrations of sucrose and glucose obtained by applying the present invention to the spectra of the mixtures shown in FIG. 4.
Figure 6B:
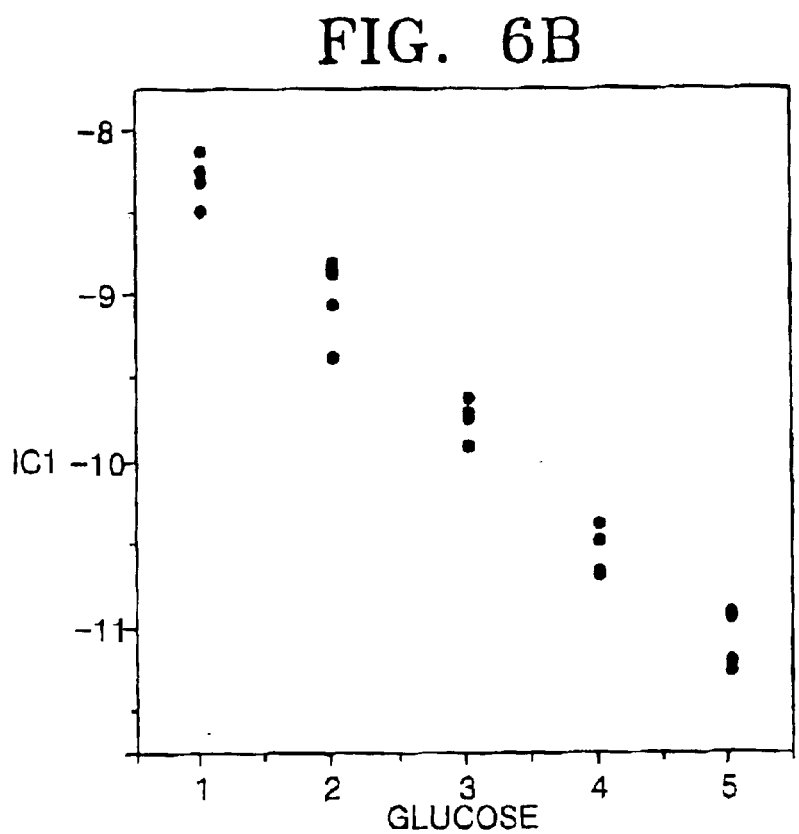

The spectra of the twenty-five (25) mixtures as shown in FIG. 3 are analyzed using the PCA and the ICA. Thus, the pure spectra of the glucose and sucrose are obtained as shown in graph G2 of FIGS. 5A and 5B, respectively. Graph G2 is similar to graph G1, which shows the actual pure spectrum of each of the glucose and sucrose. In addition, as shown in FIGS. 6A and 6B, the independent components IC1 and IC2, obtained by applying the PCA and the ICA to the spectra of the twenty-five (25) mixtures, are in a linear relationship with the concentrations of the glucose and the sucrose.

In addition, the method of the present invention may be embodied as a computer program on a computer-readable medium. For example, the method of estimating the pure spectrum and the concentration of each component from n sample mixtures, in which p kinds of components are mixed to have different concentrations, may be embodied as a first program for performing a principal component analysis (PCA) of the spectra of the n mixtures, measured using m wavelengths, to represent the spectra as factors and scores of the respective factors, and a second program for performing an independent component analysis (ICA) of the scores produced by the first program to decompose the scores into a mixing matrix and independent components, estimating the product of the factor obtained by the first program and the mixing matrix as a pure spectrum of each component, and estimating that the independent components are proportional to the concentrations of the components mixed in the mixture.

The invention may be embodied in a general purpose digital computer by running a program from a computer usable medium, including but not limited to storage media such as magnetic storage media (e.g., ROMs, floppy discs, hard discs, and the like), optically readable media (e.g., CD-ROMs, DVDs, and the like) and carrier waves (e.g., transmissions over the Internet). The computer readable recording medium can be dispersively installed in a computer system connected to a network, and stored and executed as a computer readable code by a distributed computing environment. In addition, functional programs, codes, and code segments, required for embodying the present invention, may be easily inferred by programmers skilled in the art.

As explained so far, according to an embodiment of the present invention, as long as the principal component analysis (PCA) and the independent component analysis (ICA) are applied to a spectrum of a mixture, the number of components constituting the mixture and the pure spectrum and the concentration of each component can be exactly estimated. Moreover, the method of the present invention can be applied to all types of spectral analyses, such as absorption spectrum, illumination spectrum, mass spectroscopy spectrum, magnetic resonance spectrum, and chromatography.

Preferred embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A method of estimating a pure spectrum and a concentration of each component constituting n sample mixtures, in which p kinds of components are mixed, the method comprising:

(a) performing a principal component analysis of the spectra of the n mixtures, which are measured using m wavelengths, to represent the spectra of the n mixtures as factors and scores of the respective factors, wherein n, p, and m are integers and m>p; and (b) performing an independent component analysis of the scores obtained in (a) to estimate the pure spectra and the concentrations of the respective components.

2. The method as claimed in claim 1, wherein the number of factors to be used is decided from among the factors obtained in (a) and the independent component analysis is applied to the scores of the decided factors.

3. The method as claimed in claim 2, wherein the concentrations of the components constituting the mixture are statistically independent.

4. The method as claimed in claim 1, wherein the concentrations of the components constituting the mixture are statistically independent.

5. The method as claimed in claim 1, wherein (b) comprises:

(b1) performing the independent component analysis of the scores of the factors to decompose the scores into a mixing matrix and independent components;

(b2) estimating the product of the factors obtained in (a) and the mixing matrix obtained in (b1) as the pure spectra of the respective components; and (b3) estimating the independent components obtained in step (b1) as being proportional to the concentrations of the components contained in the mixture.

6. The method as claimed in claim 1, wherein (b) comprises:

(b1) deciding the number of the factors to be used from among the factors obtained in (a);

(b2) performing the independent component analysis of the scores of the decided factors to decompose the scores into a mixing matrix and independent components;

(b3) estimating the product of the decided factor and the mixing matrix obtained in (b2) as the pure spectrum of each component; and (b4) estimating the independent components obtained in (b2) as being proportional to the concentrations of the components contained in the mixture.

7. The method as claimed in claim 1, wherein the ICA may be performed using a technique selected from the group consisting of: maximization of non-gaussianity (MN), maximum likelihood estimation (MLE), and minimization of mutual information (MMI).

8. The method as claimed in claim 1, wherein in (a), a low-noise band including information on a component to be estimated is decided as an analysis band from among the spectra of the n mixtures measured using m wavelengths.

9. The method as claimed in claim 1, wherein (a) comprises:

performing a preprocessing step to remove scattering and noise, before performing the principal component analysis of the spectra of the n mixtures measured using m wavelengths.

10. The method as claimed in claim 9, wherein the preprocessing step comprises a technique selected from the group consisting of multiplicative scatter correction (MSC), mean-centering, and autoscaling.

11. A computer-readable medium having embodied thereon a program, the program comprising:

a first program for performing a principal component analysis of a spectra of n mixtures measured using m wavelengths to represent the spectra as factors and scores of the respective factors, wherein n and m are integers; and a second program for performing an independent component analysis of the scores produced by the first program to decompose the scores into a mixing matrix and independent components, estimating that the product of the factor obtained by the first program and the mixing matrix is the pure spectra of each component, and estimating that the independent components are proportional to the concentrations of the components contained in the mixture.

12. The medium as claimed in claim 11, wherein the concentrations of the components constituting the mixture are statistically independent.

13. An apparatus of estimating a pure spectrum and a concentration of each component constituting n sample mixtures, in which p kinds of components are mixed, the apparatus comprising:

a principal component analysis unit for performing a principal component analysis of the spectra of the n mixtures, which are measured using m wavelengths, to represent the spectra of the n mixtures as factors and scores of the respective factors, where n, m, and p are integers and $m>p$;

an independent component analysis unit for performing an independent component analysis of the scores provided from the principal component analysis unit, to decompose the scores into a mixing matrix and independent components;

a pure spectrum estimating unit for estimating the product of the factor provided from the principal component analysis unit and the mixing matrix as the pure spectra of each component; and a concentration estimating unit for estimating the independent components as the concentrations of the components contained in the mixture.

* * * * *